(12) United States Patent
Lin et al.

(10) Patent No.: US 9,757,392 B2
(45) Date of Patent: Sep. 12, 2017

(54) PHARMACEUTICAL COMPOSITION AND EXTRACT OF PORIA FOR ENHANCING UPTAKE OF NUTRIENTS

(75) Inventors: Hang-Ching Lin, Taipei (TW); Tsu-Chung Chang, Taipei (TW); Wen-Liang Chang, Taipei (TW); Yi-Yang Song, Pingtung (TW)

(73) Assignee: Sinphar Pharmaceutical Co., Ltd., I Lan (TW)

( * ) Notice: Subject to any disclaimer, the term of this patent is extended or adjusted under 35 U.S.C. 154(b) by 862 days.

(21) Appl. No.: 12/415,205

(22) Filed: Mar. 31, 2009

(65) Prior Publication Data
US 2009/0247496 A1    Oct. 1, 2009

(30) Foreign Application Priority Data
Mar. 31, 2008  (TW) .............................. 97111791 A

(51) Int. Cl.
| | | |
|---|---|---|
| A61K 9/00 | (2006.01) | |
| A61K 31/56 | (2006.01) | |
| A61K 31/575 | (2006.01) | |
| A61K 9/48 | (2006.01) | |
| A61K 36/076 | (2006.01) | |
| A61K 45/06 | (2006.01) | |

(52) U.S. Cl.
CPC ............ *A61K 31/575* (2013.01); *A61K 9/485* (2013.01); *A61K 9/4866* (2013.01); *A61K 36/076* (2013.01); *A61K 45/06* (2013.01)

(58) Field of Classification Search
USPC .......................................... 424/400; 514/181
See application file for complete search history.

(56) References Cited

U.S. PATENT DOCUMENTS

| | | | | |
|---|---|---|---|---|
| 5,880,114 A | * | 3/1999 | Deluca ................. | A61K 31/593 514/167 |
| 2003/0190332 A1 | * | 10/2003 | Gilad et al. ................ | 424/227.1 |
| 2004/0229852 A1 | * | 11/2004 | Lin ........................ | A61K 31/56 514/169 |
| 2006/0210546 A1 | * | 9/2006 | Sokol ................... | A61K 31/197 424/94.1 |

FOREIGN PATENT DOCUMENTS

| | | | |
|---|---|---|---|
| CN | 1079869 | * | 12/1993 |
| CN | 1124152 | * | 6/1995 |
| CN | 1233418 | * | 11/1999 |
| CN | 1923012 | * | 3/2007 |
| CN | 101130039 | * | 2/2008 |
| TW | 200744481 | * | 12/2007 |

OTHER PUBLICATIONS

Cuellar (Chem. Pharm. Bull (1997) 45:492-494).*

* cited by examiner

*Primary Examiner* — Marcos Sznaidman
(74) *Attorney, Agent, or Firm* — Cesari and McKenna, LLC

(57) ABSTRACT

The present invention discloses a novel use of a lanostane having the following formula (I) in enhancing uptake of nutrients:

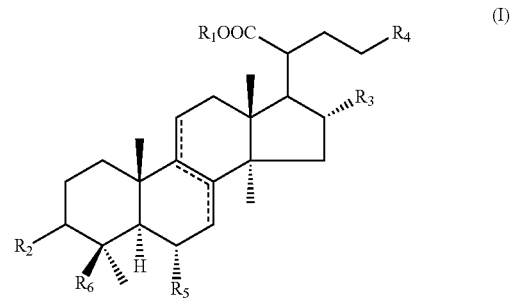

wherein $R_1$ is either H or $CH_3$; $R_2$ is $OCOCH_3$, $=O$ or OH; $R_3$ is H or OH; $R_4$ is $-C(=CH_2)-C(CH_3)_2R_a$, in which $R_a$ is H or OH, or $-CH=C(CH_3)-R_b$, in which $R_b$ is $CH_3$ or $CH_2OH$; $R_5$ is H or OH; and $R_6$ is $CH_3$ or $CH_2OH$.

14 Claims, 14 Drawing Sheets

| | |
|---|---|
| Control | Rate = 3.0420 ± 0.0605 nmol/min |
| K2 (0.001 μ M) | Rate = 3.9220 ± 0.0388 nmol/min |
| K2 (0.01 μ M) | Rate = 4.1350 ± 0.0688 nmol/min |
| K2 (0.1 μ M) | Rate = 3.0860 ± 0.1104 nmol/min |
| K2 (1.0 μ M) | Rate = 2.9690 ± 0.0974 nmol/min |

| | |
|---|---|
| Control | Rate = 3.0420 ± 0.0605 nmol/min |
| K3 (0.001 μM) | Rate = 2.6170 ± 0.1982 nmol/min |
| K3 (0.01 μM) | Rate = 3.5970 ± 0.1285 nmol/min |
| K3 (0.1 μM) | Rate = 3.4030 ± 0.1794 nmol/min |
| K3 (1.0 μM) | Rate = 3.3490 ± 0.1940 nmol/min |

| | |
|---|---|
| Control | Rate = 3.0420 ± 0.0605 nmol/min |
| K4 (0.001 μ M) | Rate = 3.7320 ± 0.1447 nmol/min |
| K4 (0.01 μ M) | Rate = 4.1730 ± 0.0989 nmol/min |
| K4 (0.1 μ M) | Rate = 4.7450 ± 0.1745 nmol/min |
| K4 (1.0 μ M) | Rate = 3.9740 ± 0.2231 nmol/min |

Tryptophan transport of K1

| | |
|---|---|
| Control | Rate = 17.780 ± 0.501 nmol/min |
| 0.001μ M K1 | Rate = 23.550 ± 1.304 nmol/min |
| 0.01μ M K1 | Rate = 24.160 ± 1.063 nmol/min |
| 1.0μ M K1 | Rate = 21.390 ± 0.886 nmol/min |

Tryptophan transport of K4

| | |
|---|---|
| Control | Rate = 17.780 ± 0.501 nmol/min |
| 0.01μ M K4 | Rate = 15.720 ± 2.575 nmol/min |
| 0.1μ M K4 | Rate = 27.390 ± 1.818 nmol/min |
| 1.0μ M K4 | Rate = 27.200 ± 1.370 nmol/min |

| Control | Rate = 0.0759 ± 0.0169 nmol/mg/min |
| K2 (0.001 μM) | Rate = 0.1094 ± 0.0194 nmol/mg/min |
| K2 (0.1 μM) | Rate = 0.1083 ± 0.0280 nmol/mg/min |

| Control | Rate = 0.0759 ± 0.0169 nmol/mg/min |
| K4 (0.001 μM) | Rate = 0.0665 ± 0.0126 nmol/mg/min |
| K4 (0.1 μM) | Rate = 0.0852 ± 0.0174 nmol/mg/min |

PHARMACEUTICAL COMPOSITION AND EXTRACT OF *PORIA* FOR ENHANCING UPTAKE OF NUTRIENTS

CROSS-REFERENCE TO RELATED APPLICATION PARAGRAPH

This application claims the benefit of Taiwanese Application No. 97111791 filed on Mar. 31, 2008, the content of which is hereby incorporated by reference in its entirety.

FIELD OF THE INVENTION

The present invention relates to a novel use of lanostane compounds in enhancing uptake of nutrients, and more particularly to a pharmaceutical composition for enhancing uptake of nutrients comprising a lanostane compound as a potent component.

DESCRIPTION OF PRIOR ART

US 2004/0229852 A1 discloses a pharmaceutical composition useful in enhancing immunity of human body. The composition contains potent components of lanostane compounds. A method is devised to obtain an extract from metabolite, sclerotium, or fermentation product of *Poria cocos* (Schw) Wolf. The extract contains 5-60% of the lanostane compounds by weight of the extract. The extract is devoid of secolanostane capable of inhibiting immunity development.

Generally speaking, the uptake of nutrients is vital in keeping the human body healthy and vigorous. The thorough uptake of nutrients in the gastrointestinal tract allows the nutrients to be utilized by a variety of cells in the human body, which builds a strong foundation for a healthy human body. For example, glucose may be transformed into ATP (adenosine triphosphate) by human cells, and the cells then utilize ATP to carry out normal functions of tissue organs, such as beatings of the heart, neural transmission, and actions of skeletal muscles. Therefore, the search for any substances or methods for enhancing uptake of nutrients has become an important issue for researchers and ordinary people alike.

SUMMARY OF THE INVENTION

A primary objective of the present invention is to provide a novel use of lanostane compounds in enhancing uptake of nutrients.

Another objective of the present invention is to use lanostane compounds as food or beverage additives for enhancing uptake of nutrients.

Another objective of the present invention is to provide a pharmaceutical composition for enhancing uptake of nutrients comprising a lanostane compound as a potent component. The "pharmaceutical composition" described herein refers not only to concoctions conforming to literal meanings thereof, but further includes nutritional supplementary compositions. The nutritional supplementary compositions comprise not only nutrients, but also a lanostane compound as a potent component for promoting uptake of nutrients.

A pharmaceutical composition capable of enhancing uptake of nutrients of a mammal (for example, a human), which comprises an amount effective for enhancing nutrition uptake of a lanostane having the following chemical formula (I) as an active ingredient:

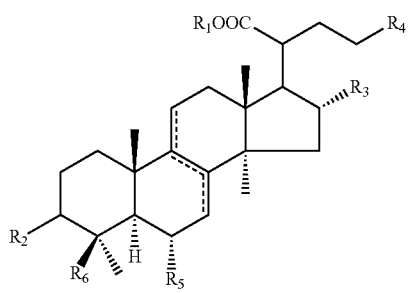

(I)

wherein $R_1$ is either H or $CH_3$; $R_2$ is $OCOCH_3$, =O or OH; $R_3$ is H or OH; $R_4$ is —C(=$CH_2$)—C($CH_3$)$_2R_a$, in which $R_a$ is H or OH, or —CH=C($CH_3$)—$R_b$, in which $R_b$ is $CH_3$ or $CH_2OH$; $R_5$ is H or OH; and $R_6$ is $CH_3$ or $CH_2OH$, or a pharmaceutically acceptable salt thereof.

Preferably, the lanostane having the following chemical formula (I) is

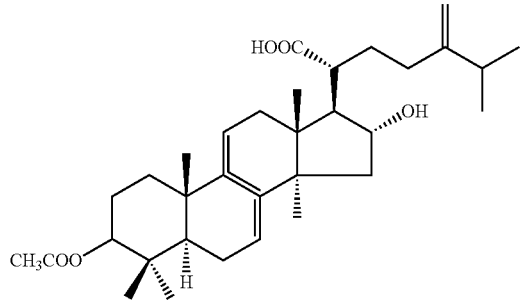

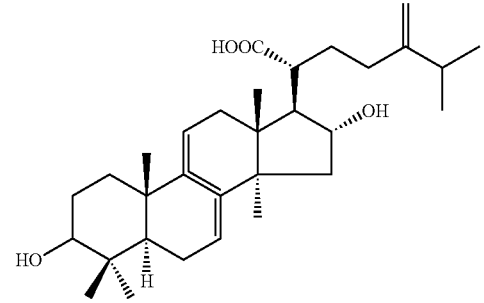

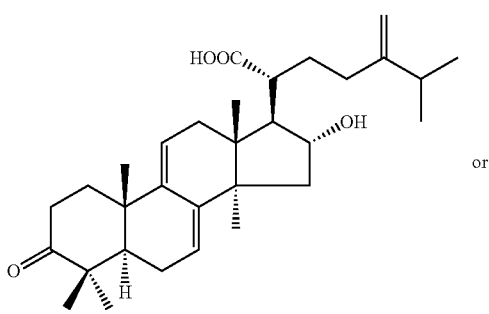

or

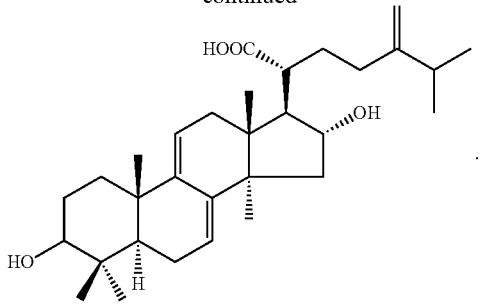

Preferably, the pharmaceutical composition comprises 0.1-20% of the lanostane (I) or a pharmaceutically acceptable salt thereof by weight of the composition.

Preferably, the pharmaceutical composition is orally administered.

Preferably, the pharmaceutical composition comprises a Poria extract, said Poria extract comprising 1-60% of the lanostane (I) by weight of the extract, and being substantially devoid of secolanostane.

Preferably, said Poria extract is prepared by a method comprising the following steps:
a) extracting metabolites, fermentation products or sclerotium of Poria cocos (Schw) Wolf by water, methanol, ethanol, or a mixed solvent thereof;
b) concentrating the resulting liquid extract from step a);
c) introducing the resulting concentrated substance from step b) into a silica gel column;
d) eluting the silica gel column with an eluent having a low polarity, and collecting the resulting eluate; and
e) concentrating the eluate to form a concentrated eluate.

Preferably, the concentrated eluate from step e) has a chromatographic value, Rf, not less than 0.1 in accordance with a thin layer chromatography, which is developed by a mixed solvent of dichloromethane:methanol=96:4 and is detected by an ultraviolet lamp and iodine vapor.

Preferably, the extraction in step a) is carried out by using 95% ethanol.

Preferably, the extraction in step a) comprises extracting metabolites, fermentation products or sclerotium of Poria cocos (Schw) Wolf by boiling water; adding a base to the resulting extraction aqueous solution until a pH value thereof is 9-11; recovering the basic aqueous solution; adding an acid to the basic aqueous solution until a pH value thereof is 4-6 to form a precipitate; recovering the precipitate; extracting the precipitate with ethanol; and recovering a liquid extract.

Preferably, the concentrated substance resulted from step b) is further extracted with a two-phase solvent containing methanol and n-hexane in a volumetric ratio of 1:1, a methanol layer is separated from the two-phase solvent extraction mixture, and the methanol layer is concentrated to form a concentrate, which is used as a feed to the silica gel column in step c).

Preferably, the low polarity eluent in step d) is a mixed solvent containing dichloromethane and methanol in a volumetric ratio of 96.5:3.5.

Preferably, said Poria extract comprises 5-35% of the lanostane (I).

Preferably, the composition of the present invention further comprises a nutrient, for examples glucose, an amino acid, a vitamin, or a combination thereof.

A further objective of the present invention is to provide a method for enhancing uptake of nutrients of a mammal (for example, a human), which comprises administering to the mammal an amount effective for enhancing nutrition uptake of the lanostane having the chemical formula (I) or a pharmaceutically acceptable salt thereof as an active ingredient.

Still a further objective of the present invention is to provide a method for enhancing uptake of nutrients of a mammal (for example, a human), which comprises administering to the mammal an amount effective for enhancing nutrition uptake of the aforesaid Poria extract as an active ingredient.

In the present invention, the lanostane having the formula (I) or a pharmaceutically acceptable salt thereof, or the aforesaid Poria extract for use in enhancing uptake of nutrients as an active ingredient may be applied in following circumstances: (1) For elevating the nutritional status of elderly people; as the digestive systems in the elderly people decline in function along with the aging process, the uptake of nutrients deteriorates as a consequence, which causes malnutrition in the elderly people; uses of the active ingredient may help boost the nutritional status of elderly people. (2) For strengthening feeble children; during the developmental process, some children are inherently weaker than average and cannot be boosted in physique by increasing nutritional supplements alone, thus uses of the active ingredient may help strengthen the nutritionally disadvantaged children. (3) For people who are under constant stress or who often stay up late to work; these people often suffer from gastrointestinal problems due to disorders caused by stress, and one of the gastrointestinal problems is malabsorption syndrome, which can lead to other problems like fatigue and low energy, thus uses of the active ingredient may help alleviate such problems. (4) For athletes, laborers, and office workers who need to spend large amounts of energy or handle great workloads and need to take nutritional supplements frequently; people who work or labor excessively need to spend a large amount of energy (in the form of ATP), and has to replenish energy frequently; since energy is mainly derived from glucose in the human body, an acceleration in the replenishment of glucose promotes the production of energy, thus uses of the active ingredient would be an effective method for replenishing glucose for athletes, laborers, and workers seeking to boost self performance. (5) For physically weak patients who have undergone surgeries or cancer treatments (chemotherapy or radiation therapy), and urgently require nutritional supplements (including amino acids, glucose, and vitamins); intake of the active ingredient may help the patients recuperate quickly. (6) For people afflicted with viral diarrhea; children often become susceptible to influenza and diarrhea caused by viral infections (such as infection of rotavirus) during seasonal changes, and in severe cases, diarrhea may even cause heavy losses of water, electrolytes, nutrients and result in death; since the active ingredient of the present invention have been known to be immunity-boosting (which eliminates viruses) and may enhance uptake of nutrients, intake of the active ingredient may allow water to be absorbed along with the uptake of nutrients (which alters the osmotic pressure) and enter the human body, subsequently protect the afflicted children from further life-threatening diarrhea. In sum, the active ingredient of the present invention may be used as nutritional supplements and added into milk powders, beverages, and foods; the active ingredient of the present invention may also be applied for medical purposes and used as a medicine in admixture of a pharmaceutically acceptable carrier or diluent for the active ingredient in the form of tablets, capsules, granular dosage, liquid dosage, and injection dosage.

BRIEF DESCRIPTION OF DRAWINGS

The aforesaid objectives and advantages of the present invention will be more clearly understood when considered in conjunction with the accompanying drawings, in which.

DETAILED DESCRIPTION OF PREFERRED EMBODIMENTS

Figure 1:
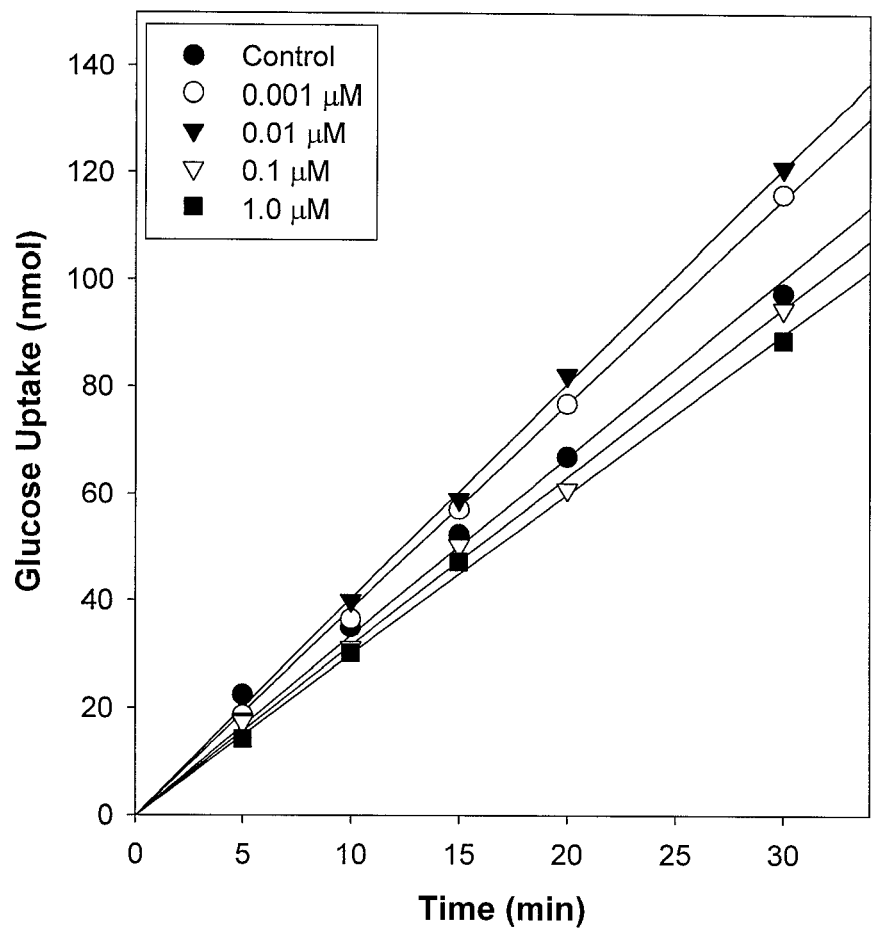
FIGS. 1 to 3 are plots that illustrate the effects the lanostane compounds K2, K3, and K4 of the present invention have on the uptake of glucose by intestinal cells (Caco-2).

Modern biochemistry has revealed that humans can obtain a variety of nutrients from foods, in which nutrients mainly needed for generating energy or maintaining cellular metabolic activities include glucose, amino acids, and vitamins. However, these nutrients cannot freely enter and exit human tissues or cells, but are instead strictly regulated by different mechanisms. The phenomenon differs from situations in which chemicals (such as medicines) are absorbed into the human body, wherein the chemicals enter and exit the human body via diffusion on the basis of concentration difference. But when nutrients are entering and exiting cells, the nutrients must be carried in and out by specific carrier proteins or channels located on the cell membrane. A case in study is provided below, in which the process of glucose absorption in human intestines is described. Firstly, the carrier proteins in the intestine are combined with sodium ions, which allow the carrier proteins to be altered structurally, subsequently opening up the portion for combining glucose. The collective combination of glucose and sodium ions with the carrier proteins lead to morphological changes of the carrier proteins, such that glucose and sodium ions may enter a cell consequently (facing cell interior). Sodium ion is the first to detach and enter the cell, which causes glucose and the related carrier protein to become unstable. Lastly, glucose also detaches and enters the cell, and the carrier protein newly devoid of glucose and sodium ion then returns to the original orientation, which faces the intestine. When the amount of glucose in the cell accumulates to a certain level, another type of carrier protein is used to allow glucose to exit the intestinal cells and enter blood vessels via concentration gradient, and this type of carrier protein belongs to the facilitated diffusion proteins.

The Caco2 cell is a cell line derived from human colon cancer; the major characteristic of this cell line is that cells may automatically and rapidly divide into cell monolayers having polarity similar to the human intestinal tract. After two to three weeks of cell cultivation, the Caco2 cells will divide into brush borders and tight junctions with high hydrolysis capability, subsequently forming cell monolayers that may block and allow particular substances to pass through. The cell monolayers consisting of the Caco2 cells have a value of electrical resistance similar to the intestinal tract, which is approximately $300\Omega$ cm$^2$. In addition, the Caco2 cell monolayers have also been proven to possess carrier proteins corresponding to a variety of nutrients, which includes the carrier proteins for amino acids, glucose, and vitamins. Therefore, the Caco2 cell monolayers are often used in researches or trials involving processing of medicines or nutrients in intestinal cells, and the subsequent results are used for elucidating the absorption of medicines or nutrients by human intestinal cells, which are readily accepted by those familiar with the related fields [Hidalgo I J, al., *Gastroenterology*, 1989; 96:736-749; Artursson P., *J Pharm Sci*, 1990; 79:476-482.].

Traditionally, when practitioners of Chinese medicine are treating particularly feeble children, elderly people weakened by age, or patients weakened by illnesses or diseases (such as cancers), the practitioners usually use potent Chinese medicines for improving or treating the above-mentioned patients, aiming to return these people to good health. However, the ways the potent Chinese medicines improve one's health are not well known; it may be that the medicines are effective because they possess essential nutrients, or the medicines are effective for enhancing uptake of nutrients, or the medicines may enhance personal health through the aforesaid two aspects. If the uptake of nutrients is enhanced via promoting mechanisms of absorption, it is still not clear which of the components are effective for affecting the carrier proteins, and relevant scientific evidence has not been found so far. Therefore, it has been proposed to use the aforesaid Caco2 cells for testing uptake of nutrients, so as to find out the effects of potent extracts of Chinese medicines and/or potent components of Chinese medicines for enhancing uptake of nutrients. When the inventor of the present invention is selecting typical potent Chinese medicines (ginseng and *Astragalus*) to be tested on the Caco2 cells; *Poria*, a untypical potent Chinese medicine, has also been tested, and it was unexpectedly found that extract of *Poria* and lanostane compounds thereof are effective for enhancing uptake of nutrients by the Caco2 cells.

An extract of *Poria* for enhancing nutrient uptake by mammals (for example, humans) disclosed in the present invention can be prepared by a process similar to that disclosed in US2004/0229852 A1, which includes extracting *Poria cocos* (Schw) Wolf with the conventional extraction methods to obtain a crude extract, separating the crude extract by chromatography into a low polarity fraction of lanostane (with an eluent of dichloromethane:methanol of 96:4) and a high polarity fraction of secolanostane (with eluents of dichloromethane:methanol of 90:10, and 0:100), wherein the lanostane fraction is detected by a thin layer chromatography having a chromatographic value, Rf, not less than 0.1 in accordance, when it is developed by a mixed solvent of dichloromethane:methanol=96:4; the Rf is less than 0.1 for the secolanostane fraction. Several lanostanes are separated from the lanostane fraction by subjecting the lanostane fraction to silica gel column chromatography eluted, wherein the eluents used are dichloromethane:methanol=97:3 to 95:5.

The following examples are provided for describing the present invention in further details, but should not be used to limit the scope of the present invention.

EXAMPLE 1

A *Poria* powder was made of 30 kilograms of the China-grown *Poria cocos* (Schw) Wolf. The *Poria* powder was extracted with 120 L 95% alcohol for 24 hours. The mixture was filtered to obtain a filtrate. The residue was extracted and filtered for another three cycles. The filtrates were combined and concentrated to bring about a dried extract in amount of 265.2 grams. The dry extract was undergone a distribution extraction with a two-phase extraction agent (n-hexane:95% methanol=1:1), and the methanol layer was removed therefrom, which is then concentrated to obtain a dry solid in an amount of 246.9 grams. A separation of the dry solid was carried out by means of a silica gel column, which was filled with silica gel 10-40 times of the weight of the dry solid. The silica gel having a diameter of 70-230 mesh was made by Merck Corporation with a code of Silica Gel 60. The column was eluted by the following eluates in sequence: a mixed solvent of dichloromethane:methanol=96:4; a mixed solvent of dichloromethane: methanol=90:10, and pure methanol. The eluates were tested by the thin layer chromatography (TLC), wherein an ultraviolet lamp and iodine vapor were used for detecting, and a mixed solvent of dichloromethane:methane=96:4 was used as a developing liquid. The eluates having similar constituents in the TLC were combined.

The elution carried out with the mixed solvent of dichloromethane:methanol=96:4 resulted in a PCM portion in amount of 78 grams. The PCM shows 6 trace points in the thin layer chromatography. The resulting eluates from the elutions carried out with the eluents of dichloromethane: methanol=90:10 and pure methanol were combined to obtain a PCW portion in amount of 168 grams.

The PCM portion was further separated by means of an eluent of dichloromethane:methanol=96.5:3.5 and the same silica gel column to obtain purified lanostane components of K1 (K1-1 and K1-2), K2 (K2-1 and K2-2), K3, K4, K4a, K4b, K5, K6a and K6b. Further details of the separation steps and identification analysis data can be seen in US2004/0229852 A1.

The aforesaid K1 to K6b compounds have the following structures:

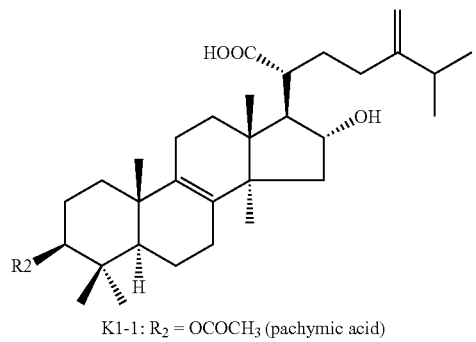

K1-1: $R_2$ = OCOCH$_3$ (pachymic acid)
K2-1: $R_2$ = OH (tumulosic acid)

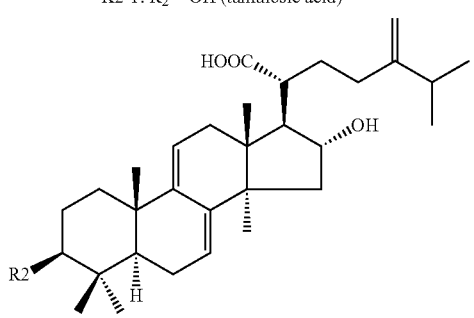

K1-2: $R_2$ = OCOCH$_3$ (trace quantity) (dehydropachymic acid)
K2-2: $R_2$ = OH (trace quantity)(dehydrotumulosic acid)

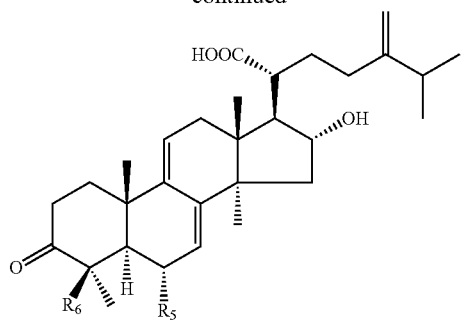

K3: $R_6$ = CH$_3$, $R_5$ = H (polyporenic acid C)
K4a: $R_6$ = CH$_2$OH, $R_5$ = H
K6a: $R_6$ = CH$_3$, $R_5$ = OH

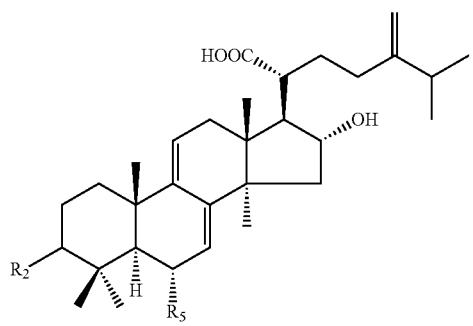

K4: $R_2$ = α-OH, $R_5$ = H (3-epihydrotumulosic acid)
K4b: $R_2$ = β-OCOCH$_3$, $R_5$ = OH

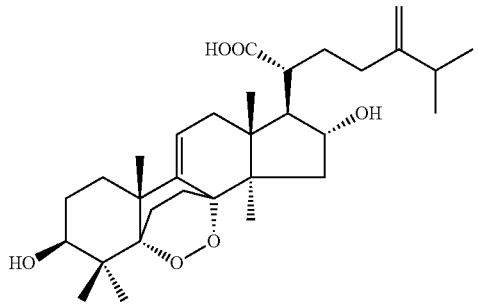

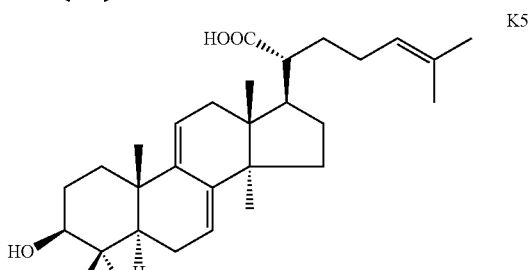

The amounts of the lanostane compounds K1 to K6b separated from the PCM portion are listed in the table below. The PCM portion contains approximately 15 wt % of the lanostane compounds K1 to K6b.

| K1 | K2 | K3 | K4 | K4a | K4b | K5 | K6a | K6b |
|---|---|---|---|---|---|---|---|---|
| 3.0 g | 6.2 g | 1.93 g | 0.55 g | 66 mg | 86.8 mg | 47.6 mg | 21.4 mg | 90.7 mg |

EXAMPLE 2

The effects the lanostane compounds K1, K2, K3, and K4, and the PCM extract prepared in Example 1 of the present invention on enhancing nutrient uptake were evaluated by the following methods.

Testing of the Cultivation of Human Caco2 Cells and Nutrient Uptake

The lanostane compounds or the PCM extract of the embodiment had been shown to enhance uptake of nutrients such as glucose, amino acids, and vitamins by the Caco2 cells in tests, wherein the Caco2 cells were inoculated on Polycarbonate Membrane Transwell® inserts (No. 3414, Corning Incorporated, NY, USA), and the cell culture media were replaced once every 2-3 days; the Caco2 cells then divided into monolayers after 14-21 days. Afterwards, the trans-epithelial electrical resistance (TEER) of the monolayers was measured by using Millicell®-ERS (Millipore EVOM-6; World Precision Instrument, Sarasota, Fla., USA), when the TEER reached 300~450 $\Omega cm^2$, and the Caco2 cells have taken the form of divided brush border, the Caco2 cells were ready for testing nutrient uptake. The Caco2 cell monolayers were cultured with cell culture media having different concentrations of nutrients to be tested for two days, wherein the used serum was always fetal bovine serum that has been treated with charcoal-dextran (CD-FBS). After two days of culturing, the cell culture was rinsed with PBS and instead cultivated with a buffer that did not contain the nutrients to be tested (for example, when glucose absorption was being tested, buffers that did not contain glucose were used) for 1 hour, and then the buffer was replaced with a fresh buffer having a predetermined concentration of particular nutrients that were radiolabeled, so as to track the rate of nutrient molecules passing through the Caco2 cell monolayers. The radiolabeled nutrients included [$^{14}$C]-D-glucose or [$^{14}$C]-D-2-deoxyglucose, [$^3$H]-L-arginine, [$^3$H]-L-tryptophan, and [$^3$H]-folic acid. In addition, the measurement of D-xylitol that has been radiolabeled with Carbon-14 or Hydrogen-3 was a mean for ensuring the integrity of the Caco2 cell monolayers [Reference: Artursson, P., *J Pharm Sci*, 1990, 79: 476-482; Ferraris R P, et al., *Am J Physiol*, 1993, 264: G285-G293.].

Analyzing Glucose Absorption

The human Caco2 cells were inoculated on Transwell inserts to allow for division into complete monolayers. Before actual measurements, the cell monolayers were treated with nutrients to be tested for two days, and then cultured with a buffer (having a composition of 80 mM NaCl, 100 mM mannitol, 20 mM Tris-HCl, pH 7.4, 3 mM $K_2HPO_4$, 1 mM $CaCl_2$, 1 mg/ml BSA) without glucose for 1 hour, the buffer at the upper cell layers was subsequently replaced with a fresh buffer having a final concentration of 10 mM gluclose, wherein 2 μCi/mL of D-glucose or D-deoxyglucose (60 mCi/mmol, American Radiolabeled Chemicals, St. Louis, Mo., USA) that had been radiolabeled with Carbon-14 was contained, such that the rate of glucose molecules passing through the Caco2 cell monolayers may be tracked. 10 μL of buffer was extracted from the lower cell layers at specific time intervals to test radioactivity strength thereof; the values of the radioactivity strength were then converted to that of glucose concentration, which represented the glucose molecules concentration of the lower cell layers buffer at specific time intervals. In addition to measuring the TEER value, the test simultaneously measured the level of D-xylitol radiolabeled with Carbon-14 for ensuring the integrity of the Caco2 cell monolayers, as well as the level of L-glucose radiolabeled with Carbon-14 for gauging non-specific background values that represented glucose not absorbed via the glucose transporters. The values of radioactivity strength may be converted into ones representing the concentration of glucose molecules passing through the Caco2 cell monolayers to lower cell layers at a specific time interval. A graph was drawn basing on glucose concentrations of lower cell layers at different intervals of time, and a straight line was obtained by using the method of numerical analysis, which had a gradient representing the average rate of glucose molecules passing through the Caco2 cell monolayers; when the cell monolayers had been treated with nutrients having the aforesaid concentration. The data for the control in this test was obtained by using the cell monolayers not treated with nutrients to be tested. The aforesaid methods for measuring were mainly based on the following reference: Kimura T. et al., *J. Pharm. Pharmacol.*, 2001, 54, 213-219.

Analyzing Amino Acid Absorption

In regard to testing the absorption of amino acids like arginine and tryptophan, the Caco2 cell monolayers were initially cultured with cell culture media containing different concentrations of nutrients to be tested for two days, and then rinsed with PBS and instead cultured with a buffer (the composition for testing arginine was: 137 mM NaCl, 10 mM Hepes pH 7.4, 0.3 mM$NaH_2PO_4$, 0.3 mM $K_2HPO_4$, 5.4 mM KCl, 2.8 mM $CaCl_2$, 1 mM $MgSO_4$, and 10 mM glucose; while the composition for testing tryptophan absorption was: 137 mM choline chloride, 10 mM Hepes pH 7.4, 0.6 mM $KH_2PO_4$, 5.4 mM KCl, 2.8 mM $CaCl_2$, 1 mM $MgSO_4$, and 10 mM glucose) that did not contain said amino acids. After 1 hour of cultivation, the amino acids (L-3H-amino acid) radiolabeled with Hydrogen-3 were used to observe the influence of treating the Caco2 cell monolayers with different concentrations of nutrients had on the absorption of amino acids. In addition to measuring the TEER value, the test also measured the level of D-xylitol radiolabeled with Hydrogen-3 for ensuring the integrity of the Caco2 cell monolayers. The values of radioactivity strength may be converted into ones representing the concentration of amino acid molecules passing through the Caco2 cell monolayers to lower cell layers at a specific time interval. A graph was drawn basing on amino acid concentrations of lower cell layers at different intervals of time, and a straight line was obtained by using the method of numerical analysis, which had a gradient representing the average rate of amino acid molecules passing through the Caco2 cell monolayers; when the cell monolayers had been treated with nutrients having the aforesaid concentration. The data for the control in this test was obtained by using the cell monolayers not treated with nutrients to be tested. The aforesaid methods for measuring were mainly based on the following reference: Pan M., et al., *Am J Physiol. Gastrointest Liver Physiol* 1995, 268: G578-G585.

Analyzing Folic Acid Absorption

Inoculating the human Caco2 cells on 10-cm culture dishes, then waiting for two weeks for the division process to complete before proceeding with the measurements. Before carrying out the measurements, the cells were initially treated with nutrients of different concentrations for two days, and then cultured with a buffer (Folate transport incubation buffer (pH6.0): Hank's Balanced Salt Solution (HBSS), supplemented with 0.14 g/L $CaCl_2$, 0.1 g/L $MgCl_2$, and 0.1 g/L $MgSO_4$) without folic acid for 1 hour, which was subsequently replaced with a fresh buffer having a final concentration of 5 μM folic acid, in which 2 μCi/mL of folic acid (3,5,7,9-$^3$H-folic acid, 25 mCi/mmol, ARC, St. Louis, Mo., USA) radiolabeled with Hydrogen-3 was contained.

Afterwards, the cells were rinsed with PBS at specific time intervals, and then dissolved and broke open with 0.2 mL of 0.2 N NaOH before being collected for centrifugation. A fixed amount of the resulted supernatant fluid was then extracted for measuring protein concentrations, while 20 μL of the supernatant fluid was extracted for measuring the concentration of folic acid molecules that had been absorbed into and accumulated in the Caco2 cells. The calculated values represented the concentration of folic acid molecules in the cell fluids of the Caco2 cells having equivalent protein mass at different specific time intervals. A graph was drawn basing on folic acid concentrations in cells at different time intervals, and a straight line was obtained by using the method of numerical analysis, which had a gradient representing the average rate of folic acid molecules being absorbed into the Caco2 cells; when the cells had been treated with nutrients having the aforesaid concentration. The data for the control in this test was obtained by using the cell monolayers not treated with nutrients to be tested. The aforesaid methods for measuring were mainly based on the following reference: Dudeja P K., et al., *Am J Physiol Gastrointest Liver Physi*, 2001, 281(1): G54-G60.

Results (1) The effect the PCM extract prepared in Example 1 on enhancing the uptake of 2-deoxyglucose by the Caco2 cells is shown in Table 1. Table 1 shows that the PCM extract is very effective for enhancing the uptake of 2-deoxyglucose by the Caco2 cells at low dosage (0.0033 μg/cc).

TABLE 1

Effect the PCM extract on the uptake of 2-deoxyglucose by the Caco2 cells

|  | Transport rate (nmol/min) | Percentage (%) |
|---|---|---|
| Control | 4.7 ± 0.29 | 100.00 |
| PCM1, 0.033 μg/cc* | 5.35 ± 0.41 | 113.74 |
| PCM2, 0.0033 μg/cc* | 7.61 ± 0.56 | 161.57 |

*The PCM extract prepared in Example 1 was adjusted to have concentrations of lanostane compounds at 0.033 μg/cc (PCM1) and at 0.0033 μg/cc (PCM2).

Figure 2:
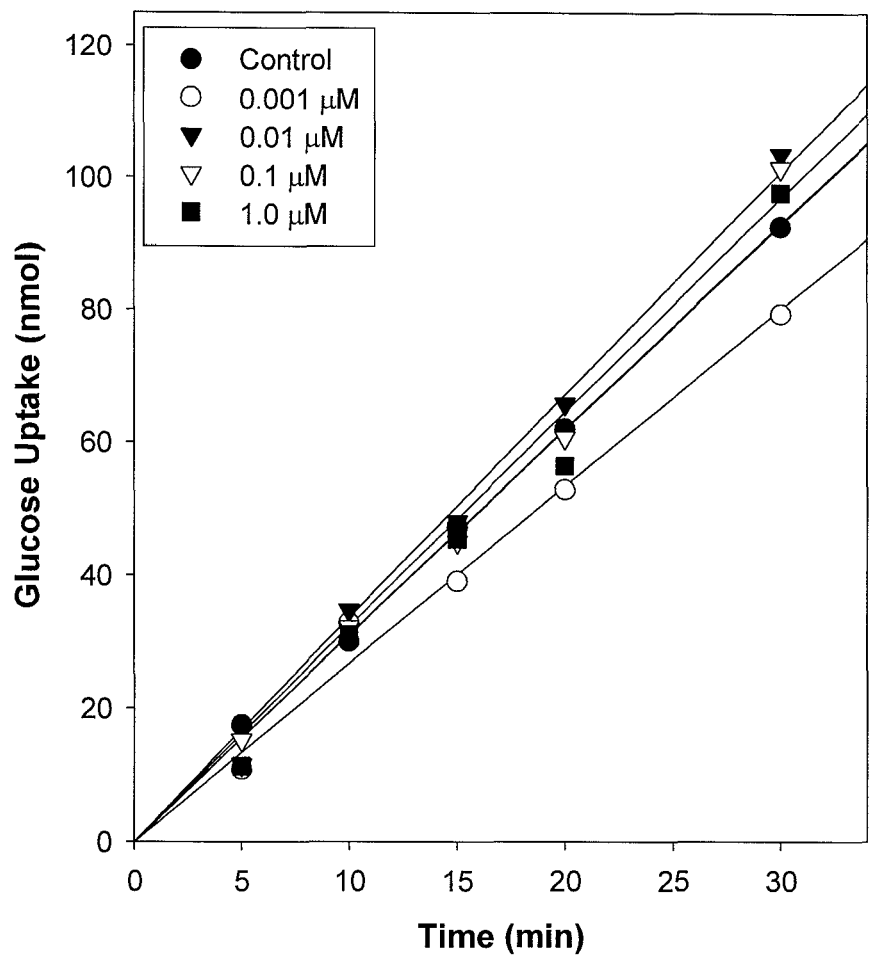
Figure 3:
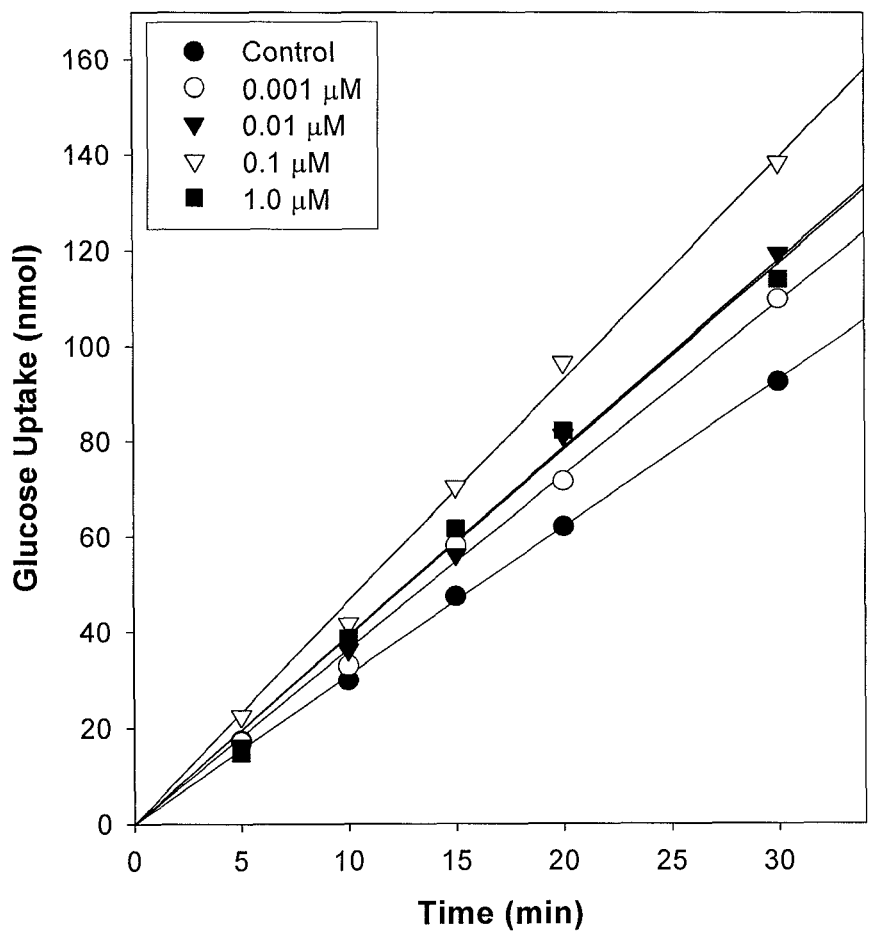
Figure 4:
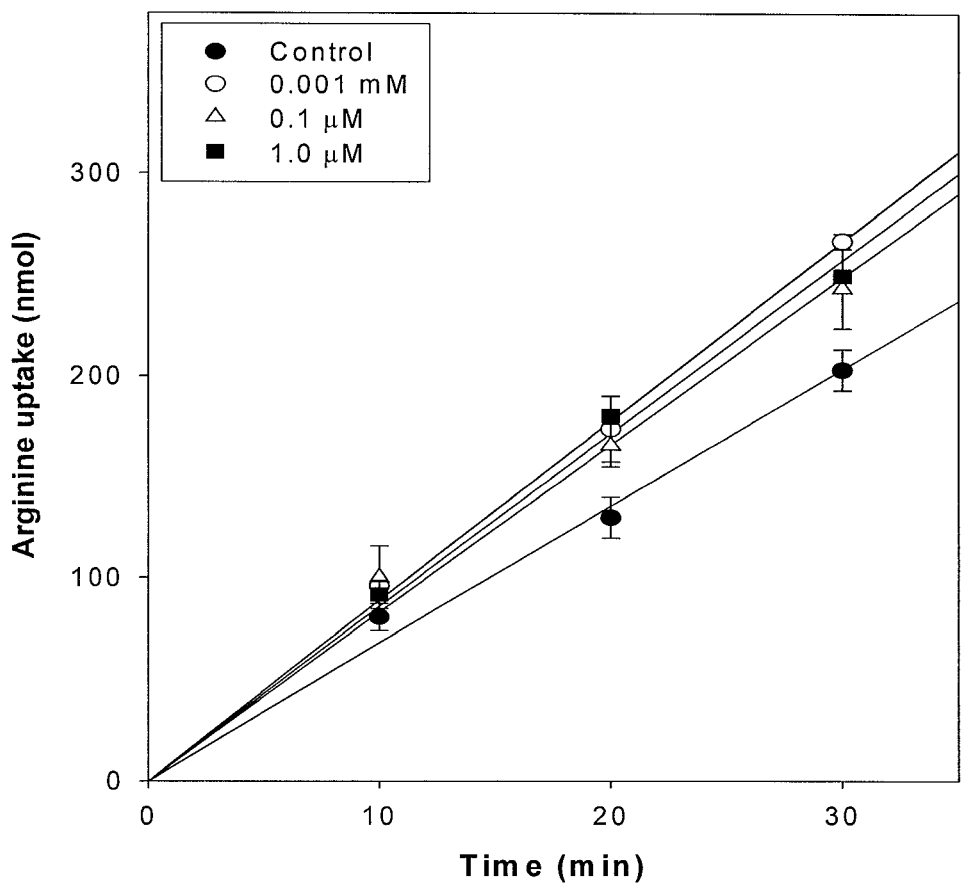
FIGS. 4 to 7 are plots that show the effects the lanostane compounds K1, K2, K3, and K4 of the present invention have on the uptake of arginine by intestinal cells (Caco-2).
Figure 5:
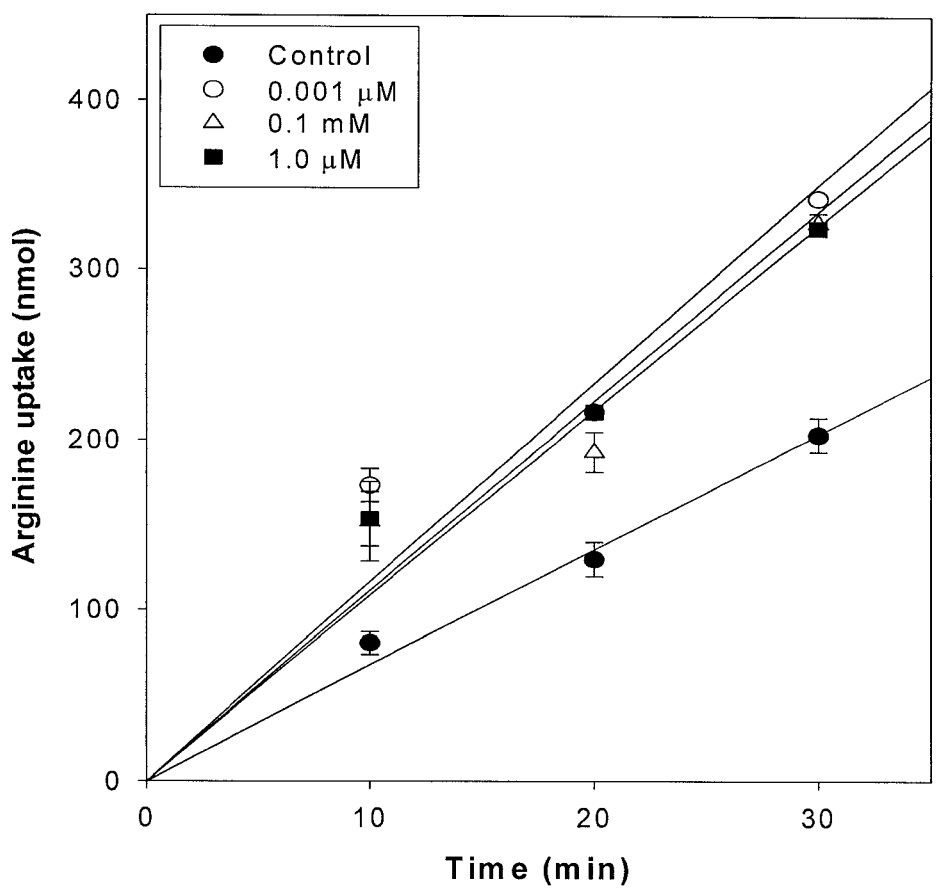
Figure 6:
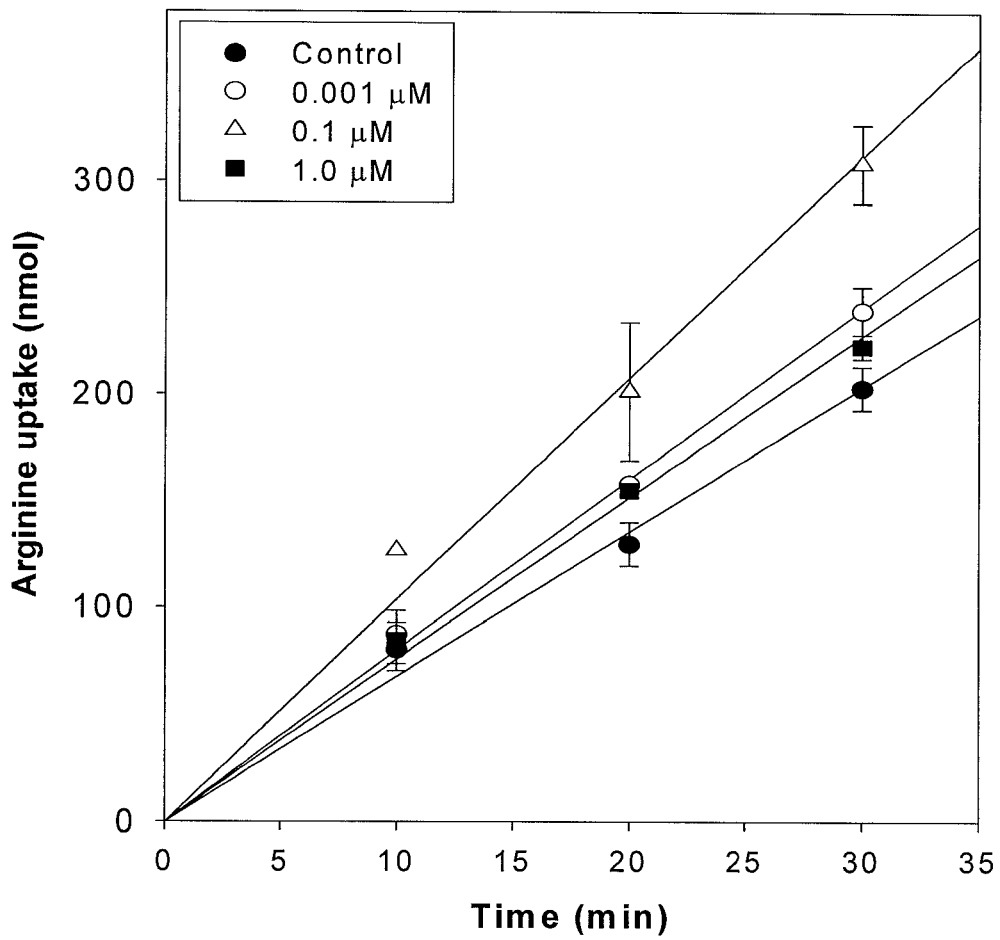
Figure 7:
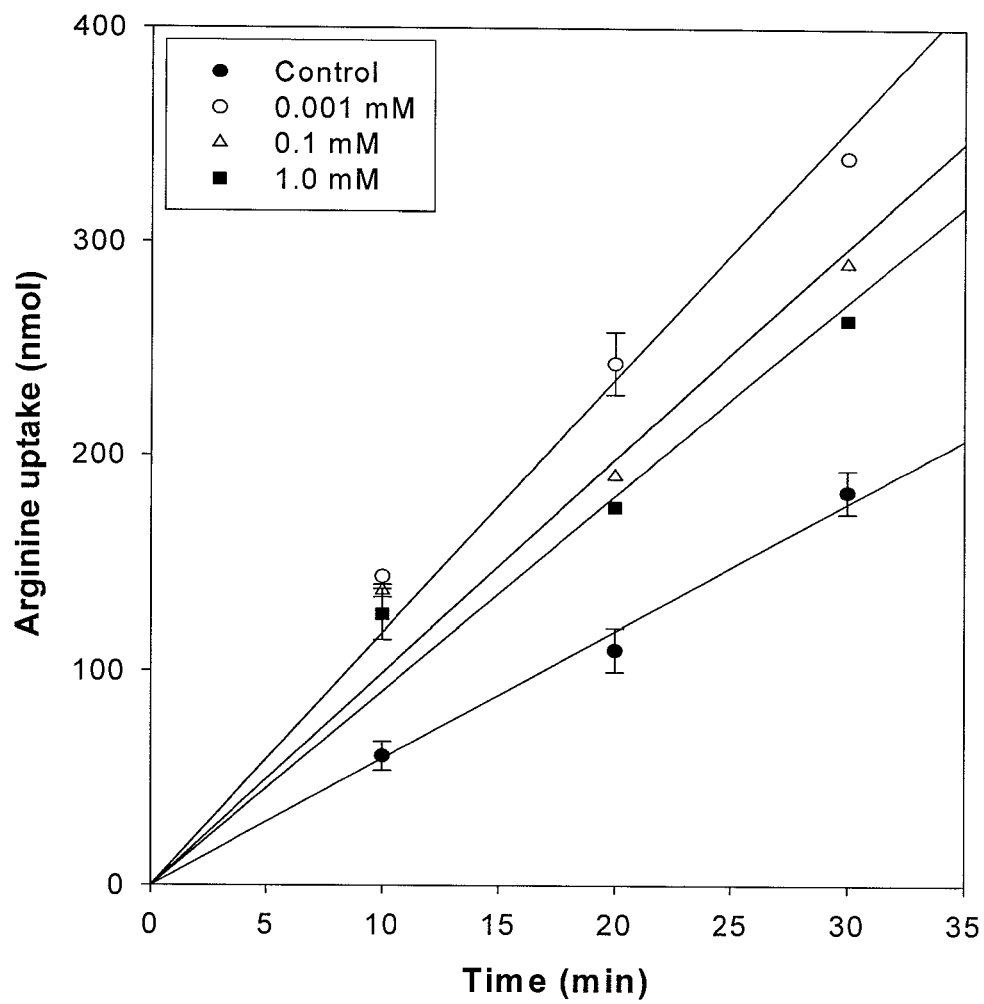
Figure 8:
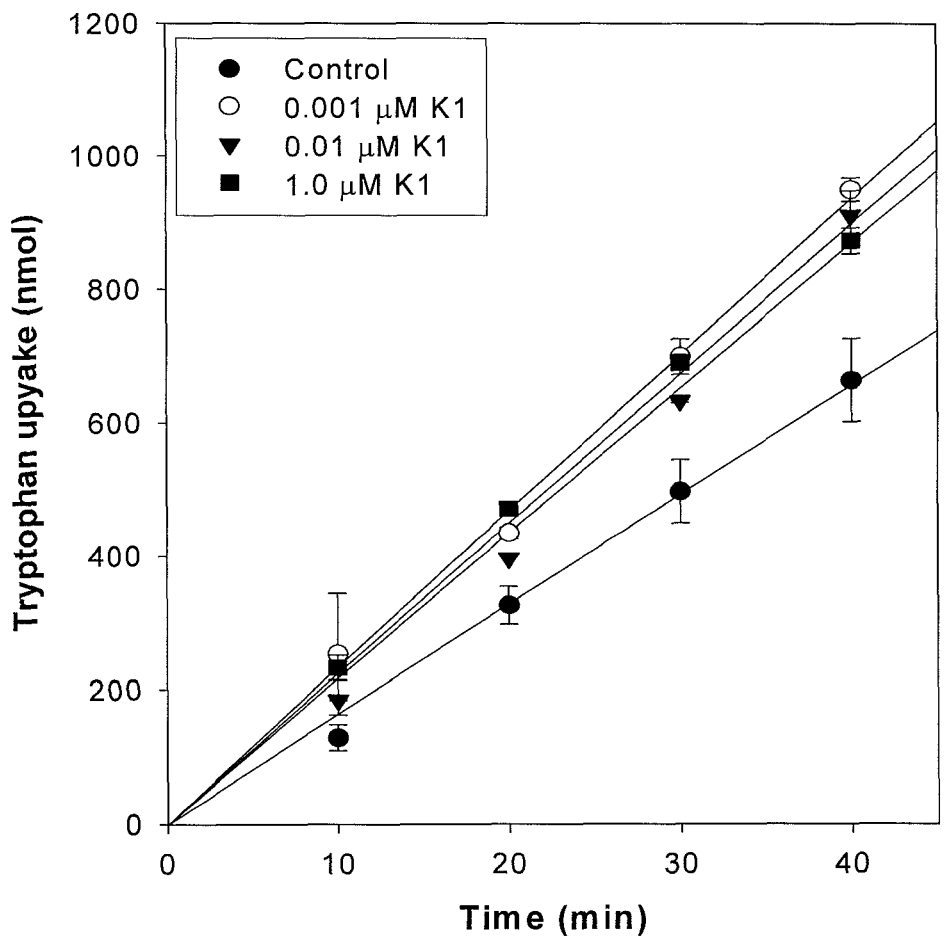
FIGS. 8 to 10 are plots that show the effects the lanostane compounds K1, K3, and K4 of the present invention have on the uptake of tryptophan by intestinal cells (Caco-2).
Figure 9:
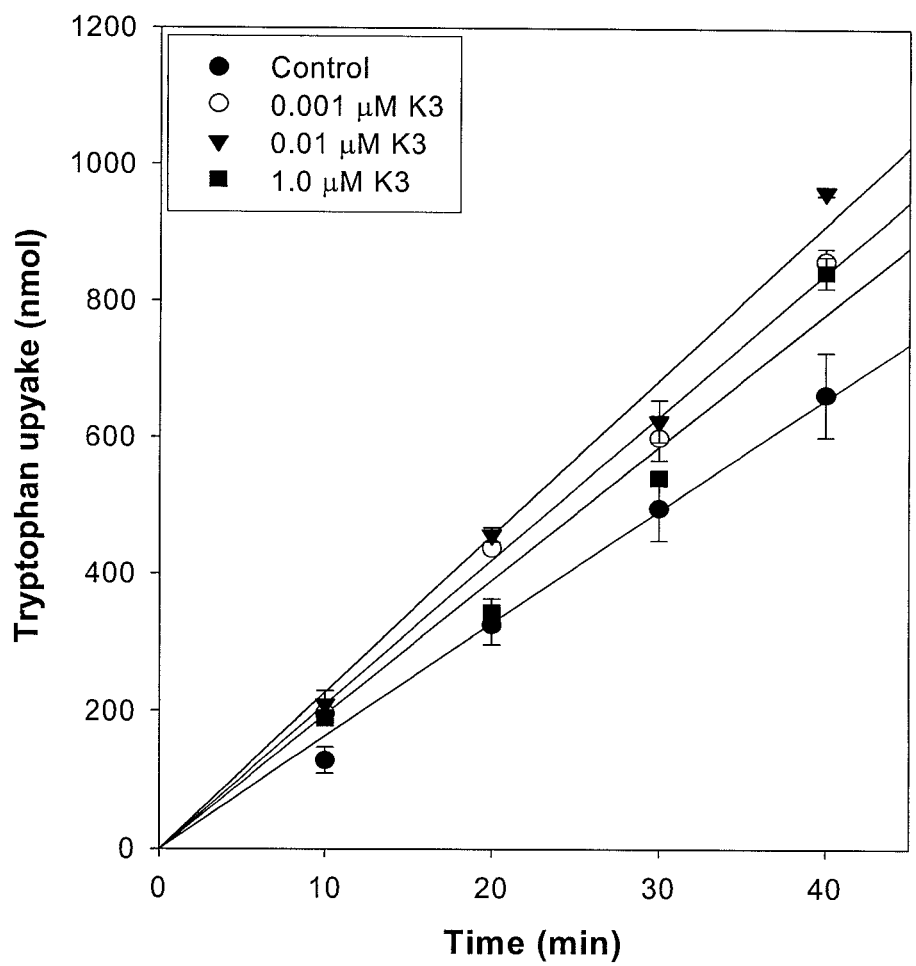
Figure 10:
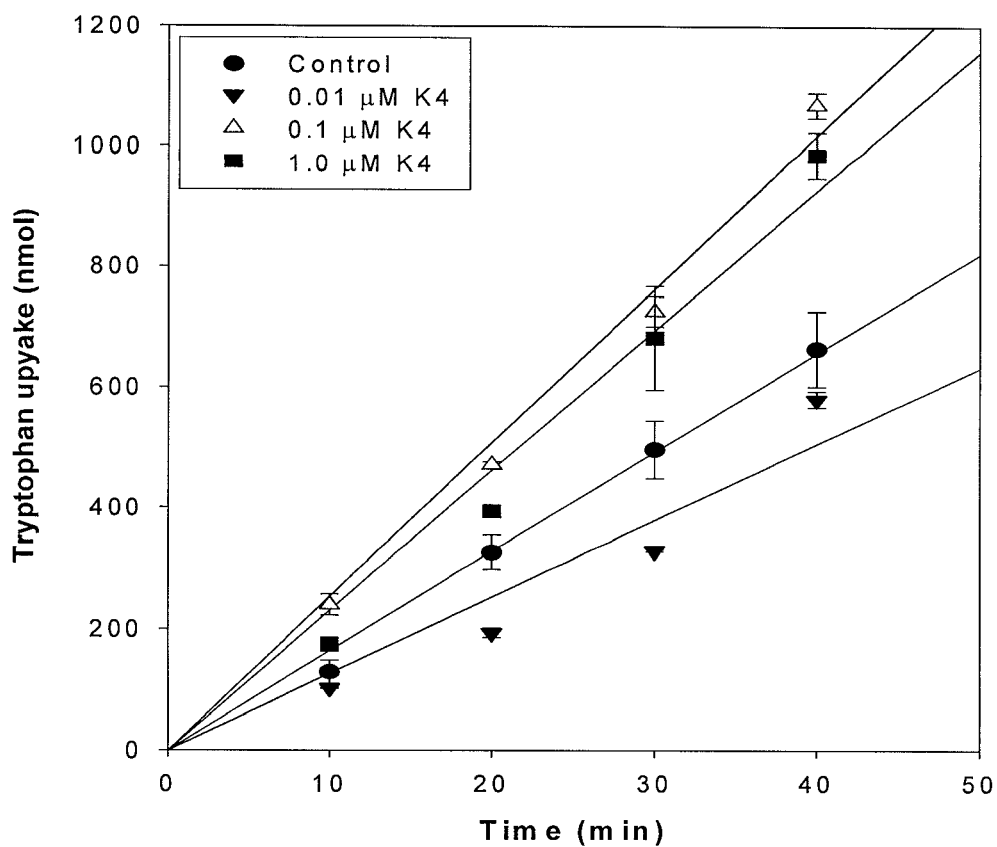
Figure 11:
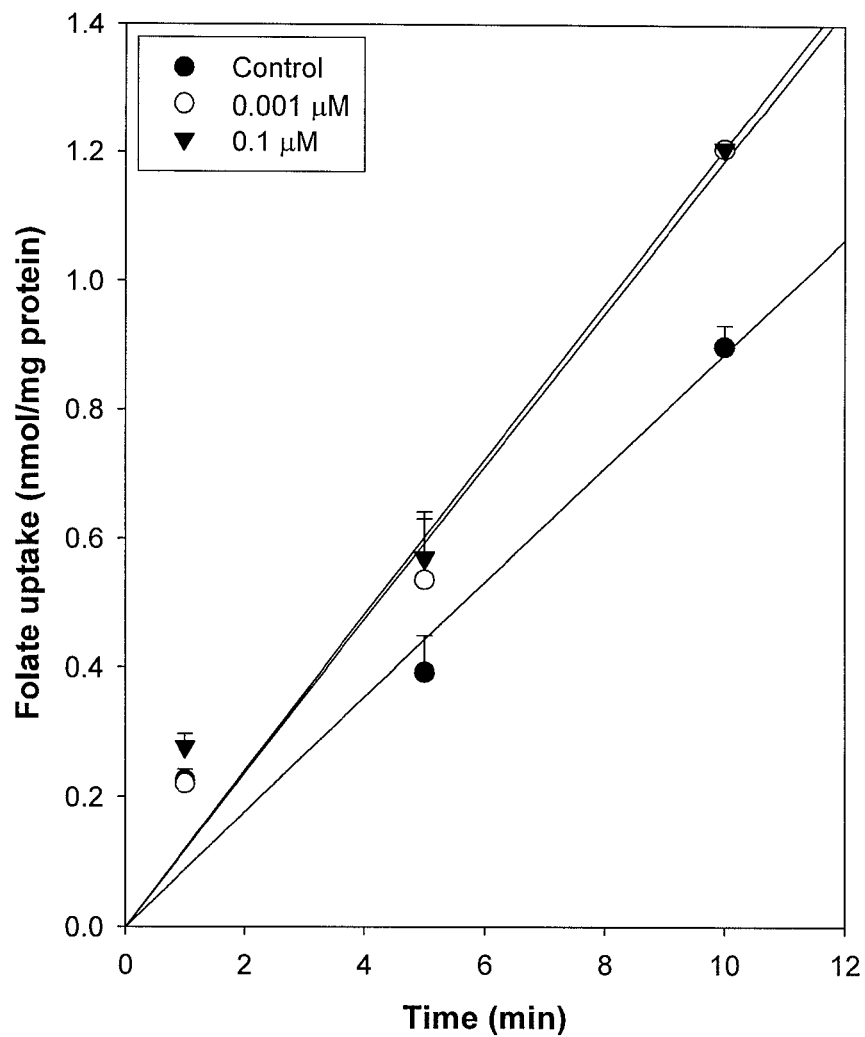
FIGS. 11 to 14 are plots that illustrate the effects the lanostane compounds K1, K2, K3, and K4 of the present invention have on the uptake of folic acid by intestinal cells (Caco-2).
Figure 12:
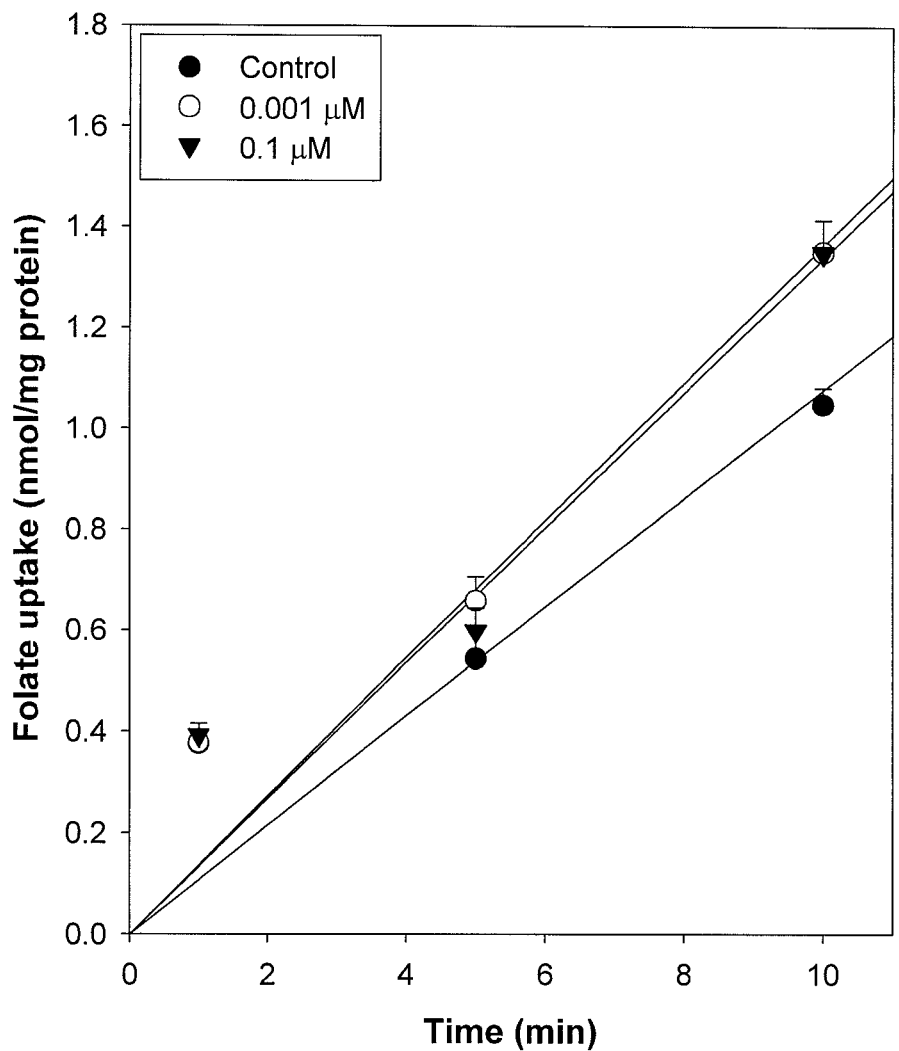
Figure 13:
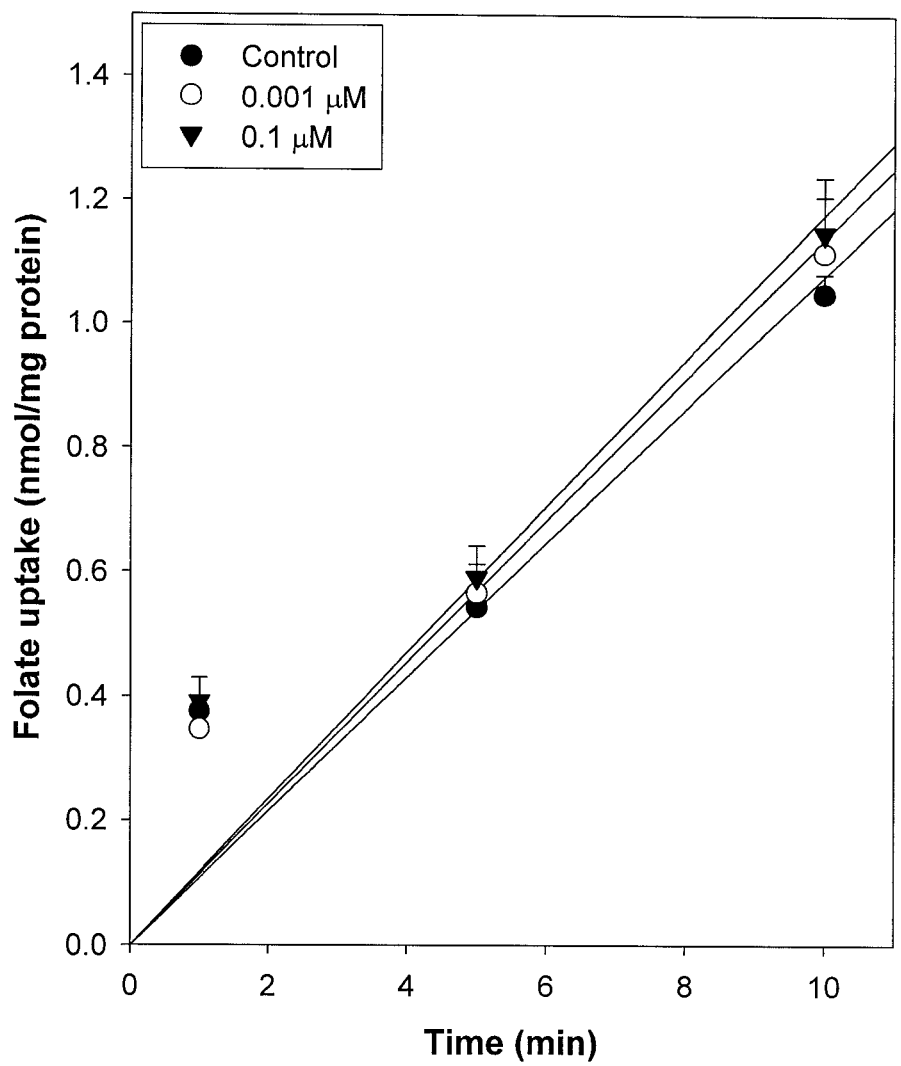
Figure 14:
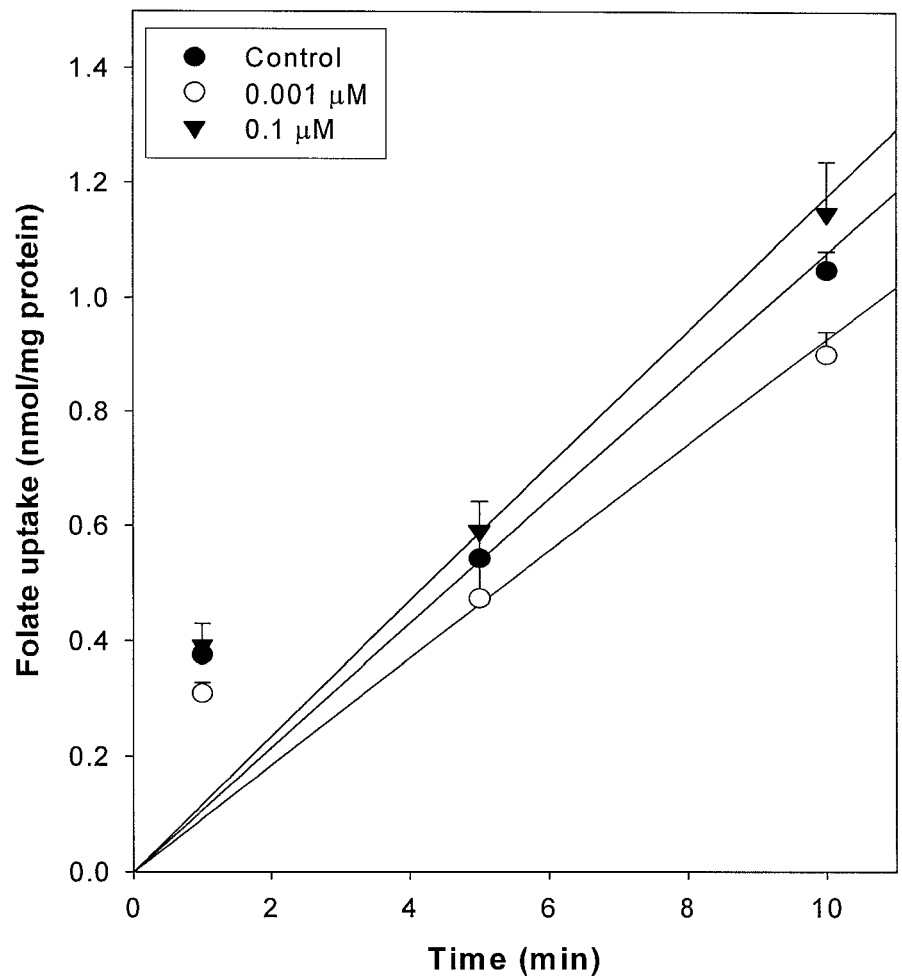

(2) The effects the lanostane compounds K1, K2, K3, and K4 prepared in Example 1 on uptake of glucose by the Caco2 cells are shown in Table 2, and FIGS. 1 to 3. Table 2 indicates that at low dosages (1 μM-0.001 μM), the lanostane compounds K2, K3, and K4 are effective for enhancing the uptake of glucose by the Caco2 cells. FIGS. 1 and 3 show that the lanostane compounds K2 and K4 are effective for enhancing glucose absorption, and the absorption rate has a linear relationship with time. The linear relationship indicates that components of *Poria* might have enhanced glucose absorption by affecting or increasing related carrier proteins. Though the lanostane compound K1 does not appear to be effective, K1 is a prodrug of K2, and may be readily transformed into K2 and become effective in the intestines or blood streams.

TABLE 2

Effects of lanostane compounds on uptake of glucose by the Caco2 cells

| Compounds[1] (μM) | | Transport rate[2] (nmol/min) | Percentage (%) | Effects |
|---|---|---|---|---|
| Control | | 3.0420 ± 0.0605 | 100.00 | — |
| K2 | 0.001 | 3.9220 ± 0.0388 | 128.93 | ↑ |
|  | 0.01 | 4.1350 ± 0.0688 | 135.93 | ↑ |

TABLE 2-continued

Effects of lanostane compounds on uptake of glucose by the Caco2 cells

| Compounds[1] (μM) | | Transport rate[2] (nmol/min) | Percentage (%) | Effects |
|---|---|---|---|---|
|  | 0.1 | 3.0860 ± 0.1104 | 101.45 | — |
|  | 1.0 | 2.9690 ± 0.0974 | 97.60 | — |
| K3 | 0.001 | 2.6170 ± 0.1982 | 86.03 | — |
|  | 0.01 | 3.5970 ± 0.1285 | 118.24 | ↑ |
|  | 0.1 | 3.4030 ± 0.1794 | 111.87 | ↑ |
|  | 1.0 | 3.3490 ± 0.1940 | 110.09 | ↑ |
| K4 | 0.001 | 3.7320 ± 0.1447 | 122.68 | ↑ |
|  | 0.01 | 4.1730 ± 0.0989 | 137.18 | ↑ |
|  | 0.1 | 4.7450 ± 0.1745 | 155.98 | ↑ |
|  | 1.0 | 3.9740 ± 0.2231 | 130.64 | ↑ |

[1]The results are shown with means ± SD (n = 3).

(3) The effects the lanostane compounds K1, K2, K3, and K4 prepared in Example 1 on uptake of amino acids (arginine and tryptophan) by the Caco2 cells are shown in Tables 3 and 4, and FIGS. 4 to 10. Table 3 shows that at low dosages (1 μM-0.001 μM), the lanostane compounds K1, K2, K3, and K4 are effective for enhancing the uptake of arginine by the Caco2 cells. Table 4 shows that K1, K3, and K4 are effective for enhancing tryptophan absorption by the Caco2 cells at low dosages (1 μM-0.001 μM). More importantly, the uptake of the aforesaid amino acids by the Caco2 cells are shown to be encouraged by low dosages of the lanostane compounds (1 μM-0.001 μM), and the absorption rate has a linear relationship with time, as can be observed in FIGS. 4 to 10. The linear relationship indicates that the lanostane compounds might have enhanced the uptake of the aforesaid amino acids by affecting or increasing related carrier proteins.

TABLE 3

Effects of lanostane compounds K1, K2, K3, and K4 on uptake of arginine by the Caco2 cells

| Compounds (μM) | | Transport rate[1] (nmol/min) | Percentage (%) | Effects |
|---|---|---|---|---|
| Control | | 6.1390 ± 0.6935 | 100.00 | — |
| K1 | 0.001 | 8.5490 ± 0.6102 | 139.26 | ↑ |
|  | 0.1 | 7.1640 ± 0.3526 | 113.37 | ↑ |
|  | 1.0 | 7.8920 ± 0.5695 | 128.56 | ↑ |
| K2 | 0.001 | 8.4400 ± 2.3890 | 137.48 | ↑ |
|  | 0.1 | 8.7740 ± 2.7020 | 142.92 | ↑ |
|  | 1.0 | 8.5550 ± 1.3090 | 139.35 | ↑ |
| K3 | 0.001 | 7.6100 ± 0.3255 | 123.96 | ↑ |
|  | 0.1 | 9.0900 ± 0.9357 | 148.07 | ↑ |
|  | 1.0 | 6.9050 ± 0.0814 | 112.48 | ↑ |
| K4 | 0.001 | 9.7980 ± 0.0843 | 159.60 | ↑ |
|  | 0.1 | 7.6420 ± 1.3290 | 124.48 | ↑ |
|  | 1.0 | 6.8730 ± 1.0980 | 111.96 | ↑ |

[1]The results are shown with means ± SD (n = 3).

TABLE 4

Effects of lanostane compounds K1, K2, K3, and K4 on uptake of tryptophan by the Caco2 cells

| Compounds[1] (μM) | | Transport rate[2] (nmol/min) | Percentage (%) | Effects |
|---|---|---|---|---|
| Control | | 17.780 ± 0.501 | 100.00 | — |
| K1 | 0.001 | 23.550 ± 1.304 | 132.45 | ↑ |
|  | 0.01 | 24.160 ± 1.063 | 135.88 | ↑ |
|  | 1.0 | 21.390 ± 0.886 | 120.30 | ↑ |

TABLE 4-continued

Effects of lanostane compounds K1, K2, K3, and K4 on uptake of tryptophan by the Caco2 cells

| Compounds[1] (μM) | | Transport rate[2] (nmol/min) | Percentage (%) | Effects |
|---|---|---|---|---|
| K3 | 0.001 | 21.520 ± 1.298 | 121.03 | ↑ |
|  | 0.01 | 24.220 ± 2.257 | 136.22 | ↑ |
|  | 1.0 | 21.610 ± 2.419 | 121.54 | ↑ |
| K4 | 0.01 | 15.720 ± 2.575 | 88.41 | ↓ |
|  | 0.1 | 27.390 ± 1.818 | 154.05 | ↑ |
|  | 1.0 | 27.200 ± 1.370 | 152.98 | ↑ |

[1]K2 does not have significant effects on the uptake of tryptophan by the Caco2 cells.
[2]The results are shown with means ± SD (n = 3).

(4) The effects the lanostane compounds K1, K2, K3, and K4 prepared in Example 1 on uptake of folic acid by the Caco2 cells are shown in Table 5 and FIGS. 11 to 14. As indicated in Table 5, K1, K2, K3, and K4 are effective for enhancing the uptake of folic acid by the Caco2 cells at low dosages (1 μM-0.001 μM). More importantly, the uptake of the folic acids by the Caco2 cells are shown to be encouraged by low dosages of the lanostane compounds (1 μM-0.001 μM), and the absorption rate has a linear relationship with time, as can be observed in FIGS. 11 to 14. The linear relationship indicates that the lanostane compounds might have enhanced the uptake of folic acids by affecting or increasing related carrier proteins.

TABLE 5

Effects of lanostane compounds K1, K2, K3, and K4 on uptake of folic acid by the Caco2 cells

| Compounds (μM) | | Transport rate[1] (nmol/mg/min) | Percentage (%) | Effects |
|---|---|---|---|---|
| Control |  | 0.0759 ± 0.0169 | 100.00 | – |
| K1 | 0.001 | 0.1105 ± 0.0157 | 145.59 | ↑ |
|  | 0.1 | 0.1042 ± 0.0153 | 137.29 | ↑ |
| K2 | 0.001 | 0.1094 ± 0.0194 | 144.14 | ↑ |
|  | 0.1 | 0.1083 ± 0.0280 | 142.69 | ↑ |
| K3 | 0.001 | 0.0864 ± 0.0157 | 113.83 | ↑ |
|  | 0.1 | 0.0852 ± 0.0174 | 112.25 | ↑ |
| K4 | 0.001 | 0.0665 ± 0.0126 | 87.62 | — |
|  | 0.1 | 0.0852 ± 0.0174 | 112.25 | ↑ |

[1]The results were shown with means ± SD (n = 3).

EXAMPLE 3

100 kg of *Poria* was boiled with 800 kg of water for 3 hours, then left for cooling to 50° C. and a pH value thereof was adjusted to pH 11 by using a 5N NaOH solution, followed by stirring the resulting solution for 3 hours. A centrifugation machine was used to separate the liquid from the solid, followed by adding another 800 kg of water to the separated solid. The aforesaid procedures were repeated, including adjusting pH value with NaOH to pH 11, stirring, and removing the solid by centrifugation. The two resulting liquids were combined, and then vacuum concentrated to a solution of 100 kg at 50° C., followed by the adjustment of pH value to pH 6.5 by using 3N HCl so as to produce a precipitate. Said precipitate was separated from the solution, subsequently rinsed with 40 L $H_2O$, and centrifuged in order to recover the precipitate; the precipitate was sprayed dry with 8 L of water, which yielded 380 g of powder. Afterwards, the powder was extracted three times by using 4 L of alcohol, and the extraction solutions were combined and concentrated to result in 238.9 g of alcohol extract; the extract then underwent HPLC separation, which gave 185.93 mg of K2, 20.34 mg of K3, 15.82 mg of K4, and 4.52 mg of K1 per gram of the extract. In other words, each gram of the extract has approximately 226.07 mg of lanostane compounds.

EXAMPLE 4

Capsules having the PCM portion prepared in Example 1 were prepared basing on the following composition:

| Components | Per Capsule | Per 30,000 Capsules |
|---|---|---|
| PCM prepared in Example (containing approximately 15 wt % of K1-K6 compounds) | 11.2 mg | 336.0 g |
| Sodium silicoaluminate | 5.0 mg | 150.0 g |
| Starch Potato | 378.8 mg | 11,364.0 g |
| Magnesium Sterate | 5.0 mg | 150.0 g |
| Total | 400 mg | 12,000.0 g |

The PCM portion and sodium silicoaluminate were sifted by using a #80 mesh, and the starch potato was sifted by using a #60 mesh; while magnesium sterate was sifted by using a #40 mesh. Subsequently, the aforesaid components were mixed evenly in a mixer, followed by filling the resulting mixture into No. 1 empty capsules. Each capsule contains approximately 1.68 mg (0.42 wt %) of effective components K1-K6.

Although particular embodiments of the invention have been described in details for purposes of illustration, it will be understood by one of ordinary skill in the art that numerous variations will be possible to the disclosed embodiments without going outside the scope of the invention as disclosed in the claims.

The invention claimed is:

1. A method for enhancing uptake of glucose, amino acids, or vitamins in a human in need thereof comprising:
   administering to the human a composition including glucose, amino acids, vitamins, or a combination thereof; and
   further administering a composition including a lanostane of formula (I) or a pharmaceutically acceptable salt thereof in an amount effective in increasing uptake of glucose, amino acids, or vitamins,

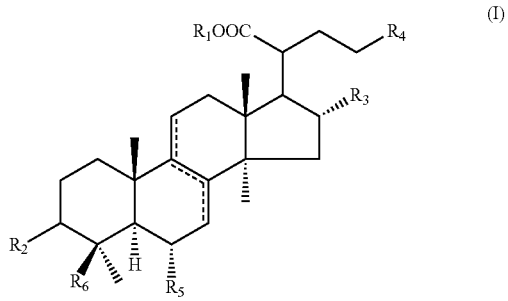

wherein $R_1$ is either H or $CH_3$; $R_2$ is $OCOCH_3$, =O or OH; $R_3$ is H or OH; $R_4$ is —C(=$CH_2$)—C($CH_3$)$_2 R_a$, in which $R_a$ is H or OH, or —CH=C($CH_3$)—$R_b$, in which $R_b$ is $CH_3$ or $CH_2OH$; $R_5$ is H or OH; $R_6$ is $CH_3$ or $CH_2OH$; and the human is in need of glucose, amino acids, or vitamins.

2. The method as defined in claim 1, wherein the lanostane is

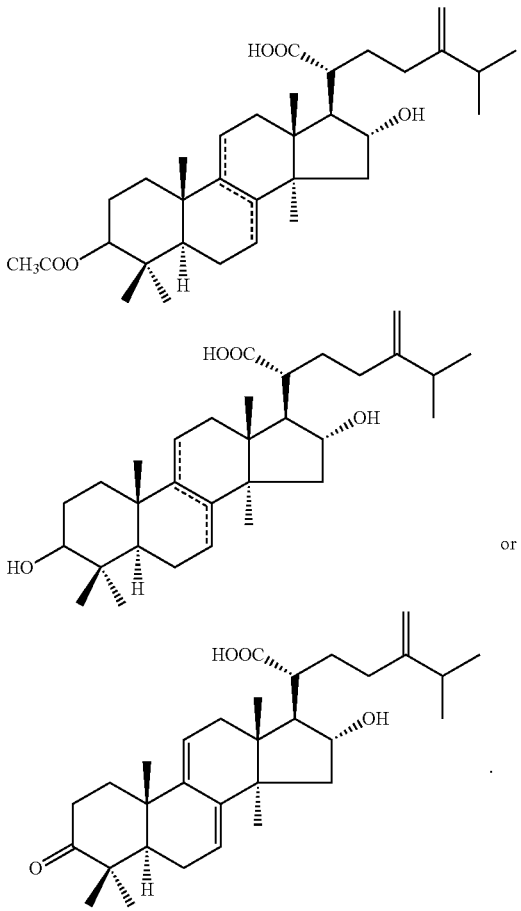

3. The method as defined in claim 1, which comprises administering to the human a pharmaceutical composition containing 0.1-20 wt % of the lanostane or a pharmaceutically acceptable salt thereof.

4. The method as defined in claim 3, wherein the pharmaceutical composition is administered to the human orally.

5. The method as defined in claim 1, wherein the lanostane is obtained by a process of extracting *Poria cocos* (Schw) Wolf.

6. The method as defined in claim 5, wherein the extracting process includes the following steps: a) extracting metabolites, fermentation products or sclerotium of *Poria cocos* (Schw) Wolf by water, methanol, ethanol, or a mixed solvent thereof; b) concentrating the resulting liquid extract from step a); c) introducing the resulting concentrated substance from step b) into a silica gel column; d) eluting the silica gel column with an eluent having a low polarity, and collecting the resulting eluate; and e) concentrating the eluate to form a concentrated eluate.

7. The method as defined in claim 6, wherein the concentrated eluate from step e) has a chromatographic value, Rf, not less than 0.1 in accordance with a thin layer chromatography, which is developed by a mixed solvent of dichloromethane:methanol=96:4 and is detected by an ultraviolet lamp and iodine vapor.

8. The method as defined in claim 6, wherein the extraction in step a) is carried out by using 95% ethanol.

9. The method as defined in claim 6, wherein the extraction in step a) comprises extracting metabolites, fermentation products or sclerotium of *Poria cocos* (Schw) Wolf by boiling water; adding a base to the resulting extraction aqueous solution until a pH value thereof is 9-11; recovering the basic aqueous solution; adding an acid to the basic aqueous solution until a pH value thereof is 4-6 to form a precipitate; recovering the precipitate; extracting the precipitate with ethanol; and recovering a liquid extract.

10. The method as defined in claim 8, wherein the concentrated substance resulting from step b) is further extracted with a two-phase solvent containing methanol and n-hexane in a volumetric ratio of 1:1, a methanol layer is separated from the two-phase solvent extraction mixture, and the methanol layer is concentrated to form a concentrate, which is used as a feed to the silica gel column in step c).

11. The method as defined in claim 9, wherein the concentrated substance resulting from step b) is further extracted with a two-phase solvent containing methanol and n-hexane in a volumetric ratio of 1:1, a methanol layer is separated from the two-phase solvent extraction mixture, and the methanol layer is concentrated to form a concentrate, which is used as a feed to the silica gel column in step c).

12. The method as defined in claim 6, wherein the low polarity eluent in step d) is a mixed solvent containing dichloromethane and methanol in a volumetric ratio of 96.5:3.5.

13. The method as defined in claim 1, which consists of administering to the human in need thereof the lanostane in the second administering step.

14. The method of claim 1, wherein the human is an athlete or worker in need of enhancing uptake of glucose, amino acids, or vitamins.

* * * * *